(12) United States Patent
Carminati et al.

(10) Patent No.: US 8,029,799 B2
(45) Date of Patent: *Oct. 4, 2011

(54) USE OF THYMOSIN ALPHA 1 FOR PREPARING A MEDICAMENT FOR THE TREATMENT OF STAGE IV MALIGNANT MELANOMA

(75) Inventors: Paolo Carminati, Milan (IT); Maria Gabriella Singrossi, legal representative, Milan (IT); Roberto Camerini, Pomezia (IT); Alfred R. Rudolph, Los Altos Hills, CA (US); Eduardo R. Martins, Foster City, CA (US)

(73) Assignee: SciClone Pharmaceuticals, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/415,589

(22) Filed: Mar. 31, 2009

(65) Prior Publication Data

US 2009/0186000 A1 Jul. 23, 2009

Related U.S. Application Data

(63) Continuation of application No. 11/734,592, filed on Apr. 12, 2007, now Pat. No. 8,017,129, and a continuation-in-part of application No. 11/424,475, filed on Jun. 15, 2006, now abandoned.

(51) Int. Cl.
*A61K 39/00* (2006.01)
(52) U.S. Cl. ..................... 424/198.1; 514/183
(58) Field of Classification Search .............. 424/198.1; 514/183
See application file for complete search history.

(56) References Cited

U.S. PATENT DOCUMENTS

| | | | |
|---|---|---|---|
| 5,861,406 A | | 1/1999 | Wehrmann |
| 5,888,980 A | * | 3/1999 | Ripka |
| 6,462,017 B1 | | 10/2002 | Rudolph et al. |
| 7,101,598 B2 | | 9/2006 | Hubbard |
| 7,297,676 B2 | | 11/2007 | Rudolph et al. |
| 2003/0185799 A1 | | 10/2003 | Rudolph |
| 2004/0235829 A1 | | 11/2004 | Scott et al. |
| 2005/0049191 A1 | | 3/2005 | Rudolph et al. |
| 2008/0300166 A1 | | 12/2008 | Tuthill et al. |
| 2010/0016211 A1 | | 1/2010 | Tuthill et al. |
| 2010/0197595 A1 | | 8/2010 | Tuthill et al. |

FOREIGN PATENT DOCUMENTS

| | | |
|---|---|---|
| AU | 2002363248 B2 | 5/2003 |
| JP | 10509955 | 9/1998 |
| WO | 9615800 A1 | 5/1996 |
| WO | 0182949 A3 | 11/2001 |

OTHER PUBLICATIONS

SciClone Press release (Dec. 2005, http://findarticles.com/p/articles/mi_pwwi/is_200512/ai_n15918545/print?tag=artBody;col1, pp. 1-3).*
Walsh (Nov. 2006, http://www.articlearchives.com/pharmaceuticals-biotechnology/pharmaceuticals/802926-1.html, pp. 1-2).*
Balch et al (J. Clin. Onc., 19(16):3635-3648, 2001.*
Lopez et al (Annals of Onc., 5:741-746, 1994).*
Ancell et al (Am J Health-Syst Pharm, 58:879-888, 2001).*
Eton et al (J. Clin. Onc., 20(8):2045-2052, 2002).*
Rasi et al (Mel. Res. 10:189-192, 2000).*
Pica et al (Anticancer Res., 18:3571-3578, 1998).*
Chadwick et al Clin. Exp. Immun. 134:477-481, 2003).*
Atallah et al (Curr. Treat. Opt. Onc., 6:185-193, May 2005).*
Billich (Curr. Opin. Inv. Drugs, 3(5):698-707, 2002).*
Avril, M.F., et al., Fotemustine Compared With DaCarbazine in Patients With Disseminated Malignant Melanoma: A Phase III Study, J. of Clinical Oncology, Mar. 15, 2004, pp. 1118-1125, vol. 22, No. 6.
Deichmann, Martin, et al., S100-Beta, Melanoma-Inhibiting Activity, and Lactate Dehydrogenase Discriminate Progressive From Nonprogressive American Joint Committee on Cancer Stage IV Melanoma, J. of Clinical Oncology, Jun. 1999, pp. 1891-1896, vol. 17, No. 6.
Eton, Omar, et al., Sequential Biochemotherapy Versus Chemotherapy for Metastatic Melanoma: Results From a Phase III Radomized Trial, J. of Clinical Oncology, Apr. 2002 pp. 2045-2052, vol. 20, No. 8.
Fink, M., et al, A phase II trial of DTIC with thalidomide (thal) in metastatic melanoma (MM), J. of Clinical Oncology, ASCO Annual Meeting Proceedings (Post-Meeting Edition), 2004, pp. 7543, vol. 22, No. 14S (Jul. 15 Supplement).
Garaci, Enrico, et al., Thymosin Alpha 1, From Bench to Bedside, Annals of the N.Y. Academy of Science, 2007, pp. 225-234, vol. 1112.
Garaci, Enrico, et al., Thymosin alpha 1 in the treatment of cancer: from basic research to clinical application, Int'l J. of Immunopharmacology, 2000, pp. 1067-1076, vol. 22.
Ishitsuka, H., et al., Protective activity of thymosin α1 against tumor progression in immunosuppressed mice, Adv. Exp. Med Biol, 1983, pp. 89-100, vol. 166.
Mackiewicz, A., et al., A first-line, phase II study with dacarbazine (DTIC) plus thymosin alpha 1 (Ta1) with or without interferon alpha (IFNa) vs. DTIC plus IFNa in stage IV melanoma, Abstracts of the Perspectives in Melanoma X and The Third Annual International Melanoma Research Congress, Sep. 2006, pp. S39, vol. 16.
Millward, M. J., et al., Randomized multinational phase 3 trial of dacarbazine (DTIC) with or without Bcl-2 antisense (oblimersen sodium) in patients (pts) with advanced malignant melanoma (MM); Analysis of long-term survival, J. of Clinical Oncology, ASCO Annual Meeting Proceedings (Post-Meeting Edition), 2004, pp. 7505, vol. 22, No. 14S (Jul. 15 Supplement).
Schadendorf, D., et al., Dacarbacine (DTIC) versus vaccination with autologus peptide-pulsed dendritic cells (DC) as first-line treatment of patients with metastatic melanoma: Results of a prospective-randomized phase III study, J. of Clinical Oncology, ASCO Annual Meeting Proceedings (Post-Meeting Edition), 2004, pp. 7508, vol. 22, No. 14S (Jul. 15 Supplement).
Therasse, Patrick, et al., New Guidelines to Evaluate the Response to Treatment in Solid Tumors, J. Nat'l Cancer Inst, 2000, pp. 205-216, vol. 92, No. 3.

(Continued)

*Primary Examiner* — Misook Yu
*Assistant Examiner* — Brad Duffy
(74) *Attorney, Agent, or Firm* — Cooley LLP

(57) ABSTRACT

It is described the use of thymosin alpha in combination with dacarbazine and optionally with Interferon alpha, for preparing a medicament for the treatment of malignant melanoma on stage IV characterized by distant unresectable metastases.

6 Claims, No Drawings

OTHER PUBLICATIONS

Third International Symposium on Combination Therapies, Institute for Advanced Studies of Immunology & Aging, Houston, TX, Oct. 29 thru 31, 1993, 2 pages.
U.S. Appl. No. 11/858,640, Non-Final Office Action mailed Apr. 15, 2009.
U.S. Appl. No. 11/858,640, Final Office Action mailed Oct. 27, 2009.
U.S. Appl. No. 11/424,475, Non-Final Office Action mailed Dec. 12, 2007.
U.S. Appl. No. 11/424,475, Final Office Action mailed May 14, 2008.
U.S. Appl. No. 11/424,475, Non-Final Office Action mailed Jan. 23, 2009.
U.S. Appl. No. 11/734,592, Non-Final Office Action mailed Dec. 13, 2007.
U.S. Appl. No. 11/734,592, Final Office Action mailed Oct. 29, 2008.
U.S. Appl. No. 11/734,592, Non-Final Office Action mailed May 19, 2009.
U.S. Appl. No. 11/734,592, Final Office Action mailed Nov. 25, 2009.
NZ Application No. 574170 Examination Report dated Jun. 4, 2010.
International Search Report with International Publication No. WO2007/144218 A1, Int'l Publication Date Dec. 21, 2007.
International Preliminary Report on Patentability for International Application No. PCT/EP2007/053712, issued Dec. 16, 2008.
IL Application No. 195955 Office Action, mailed Mar. 3, 2011.
Non-Final Office Action mailed on Aug. 2, 2010 in related U.S. Appl. No. 11/734,592.

* cited by examiner

USE OF THYMOSIN ALPHA 1 FOR PREPARING A MEDICAMENT FOR THE TREATMENT OF STAGE IV MALIGNANT MELANOMA

CROSS REFERENCE TO RELATED APPLICATIONS

This application is a continuation of U.S. application Ser. No. 11/734,592, filed Apr. 12, 2007, which is a continuation-in-part of U.S. application Ser. No. 11/424,475, filed Jun. 15, 2006, the disclosure of which is incorporated herein by reference.

BACKGROUND OF THE INVENTION

The present invention relates to the use of thymosin alpha 1 in combination with dacarbazine and optionally Interferon alpha, for preparing a medicament for the treatment of malignant melanoma on stage IV.

Melanoma is a malignant tumor of melanocytes, which are cells derived from the neural crest.

Melanomas are found primarily in normal areas of the skin, but may also occur in other mucosal surfaces.

Skin nevi may be suspected of undergoing malignant changes if they appear darker or have variable discoloration, or there is itching, an increase in size, or development of satellites.

Melanoma is unusual in that it is far more likely to metastasize than other types of cancer and can spread to regional or distant lymph nodes, or to any of the major organ systems of the body.

The most common sites of metastasis other than the skin are the lung, liver, brain, and lymph nodes.

The clinical presentation of stage IV malignant melanoma ("high-risk melanoma" or "H-RM") will vary depending on the stage and site(s) of systemic involvement.

Melanoma occurs more frequently in males and is found in adults of all ages.

The American Cancer Society ("ACS") estimated the number of new cases of all skin melanomas for 2005 at 59,580 and the number of deaths at 7,770.

HR-M accounts for approximately 22% of all cutaneous malignant melanoma cases and is associated with a high mortality rate.

Several risk factors have been identified for melanoma. It has long been believed that exposure to sunlight (i.e., ultraviolet radiation) is the primary etiological factor in the development of melanoma, which is consistent with higher incidence rates in populations with less photoprotective melanin that live closer to the equator.

Other known risk factors for melanoma include: genetics, where 5-10% of melanoma patients have a family history of the disease; dysplastic/atypical nevi; complexion (fair-skinned, red-headed or blond individuals, and individuals with a high tendency to freckle are at higher risk for developing melanoma); and history of severe blistering sunburn.

Patients diagnosed with H-RM have a strikingly worse prognosis than patients whose tumor are of minimal thickness/invasion and are locally confined.

A number of key clinical factors have been identified as prognostic indicators for melanoma, including: age; sex; characteristics of the primary tumor (e.g., anatomic location, size, Clark's level, Breslow's thickness, histopathological type, ulceration, inflammatory reaction); and lymph node involvement.

H-RM is generally a fatal disease due to the absence of adequate therapeutic options.

H-RM is characterized by tumors of the skin that metastasize to virtually every organ. The clinical presentation of H-RM varies according to the stage and site(s) of systemic involvement.

Early stage malignant melanoma without metastasis is treated by wide field surgical excision and has a high cure rate. While regional lymph node removal in addition to wide field surgical excision of the primary tumor may be successful in Stage III malignant melanoma.

In stage IV malignant melanoma, characterized by distant unresectable metastases, there is no currently available treatment. Once the metastatic process has started, the tumor becomes increasingly resistant to current methods of therapy.

Thymosin alpha 1 is a compound well known in the medical field.

Subcutaneous administration of 1 or 10 mg per day of thymosin alpha 1 to nude mice previously inoculated with human non-small cell lung cancer ("NSCLC") cells significantly decreased tumor volume.

Pulmonary metastases in mice with methylcholanthrene-induced fibrosarcoma were also reduced by thymosin alpha 1, and local sarcoma growth as well as liver and lung metastases of lymphosarcoma cells were significantly reduced in BALB/c mice treated with thymosin alpha 1.

In Int. J. Immunopharmacol. 2000; 22:1067-76 two experiences are reported:

1) The use of Dacarbazine (DTIC) (850 mg/m$^2$ i.v. on day 1)+thymosin alpha 1 (2 mg s.c. on days 4-7) in combination with interleukin-2 (18 MU/m$^2$ i.v. on days 8-12). Each cycle lasted 21 days.

2) The use of DTIC (200 mg/m$^2$ i.v. on days 1-4)+thymosin alpha 1 (1 mg s.c. on days 8-11 and 15-18) in combination with interferon alpha (3 MIU i.m. on days 11 and 18). Each cycle lasted 28 days.

These experiences showed that these treatments enhance the host immune response in patients with H-RM and prolong their survival.

Annals of Oncology. 1994; 5:741-46, relates to the use of dacarbazine (850 mg/m$^2$ i.v. on day 1) in combination with thymosin alpha 1 (2 mg s.c. on days 4-7) and IL-2 (18 MIU i.v. on days 8-12) in patients with H-RM. Each cycle lasted 21 days.

Favalli (1993; Combination Therapy in Malignant Melanoma. Third International Symposium on Combination Therapies, Houston, Tex.: Institute for Advance Studies in Immunology & Aging) teaches about the use of thymosin alpha 1 (1 mg s.c. on days 8-11 and 15-18) in combination with dacarbazine (200 mg/m$^2$ i.v. on days 1-4) and IFN-α (3 MIU i.m. on days 11 and 18) in patients with malignant melanoma. Each cycle lasted 28 days.

Current development of alternative therapies for H-RM is directed toward immunotherapies. Adjuvant immunotherapy agents designed to augment the immune response are under development and include melanoma vaccines, interferons ("IFNs"), interleukin-2 ("IL-2"), and tumor-infiltrating lymphocytes, and plasmid-based DNA vaccines.

Trials are being conducted to evaluate alternative immunotherapy agents in patients with H-RM have generally yielded less than encouraging results (Cancer Inves. 23:323-37; 2005). In general, large randomized trials have not provided any evidence of significant clinical benefit, despite the initial promising results.

While the annual incidence of malignant melanoma is on the rise, long-term studies demonstrate that current therapeutic options, for malignant melanoma on stage IV characterized by distant unresectable metastases, only produce limited results with little impact on the patient's overall survival.

Trials conducted with the interferons and interleukins in combination with dacarbazine have not demonstrated a clinical advantage over decarbazine monotherapy in advanced melanoma. Immunotherapeutic agents in combination with lymphokine-activated lymphocytes have not been found to improve response rates or affect durable remissions.

DTIC is currently the only chemotherapeutic agent approved for use in metastatic melanoma. The efficacy of dacarbazine in the treatment of metastatic melanoma is very dependent on disease site and, according to the most recent publications and abstracts (Journal of Clinical Oncology and ASCO annual meeting proceedings, 2004), the actual overall responses to DTIC are 5.5-6.8%, with responses being short-lived (i.e., three to six months). There is no evidence that these responses have any effect on the patients' overall survival.

Other drugs investigated for use alone or in combination with dacarbazine, include: alkylating agents and nitrosureas; vinca alkaloids; platinum compounds; hormonal agents; and plant-derived agents (paclitaxel (TAXOL), coumarin). None of these drugs, either alone or in combination with dacarbazine and/or Interferon alpha have been shown to be any more effective than dacarbazine alone (Cancer Medicine, Ed. 5 2000; pp. 1849-69) and are considered useful only for symptomatic relief.

In the medical field there is a pressing need to develop new therapies for stage IV malignant melanoma characterized by distant unresectable metastases.

As above mentioned to date, DTIC is currently the only chemotherapeutic agent approved for use in metastatic melanoma. The actual overall responses to DTIC are 5.5-6.8%; and there is no evidence that these responses have any effect on the patients' overall survival.

To date, the use of thymosin alpha 1 (a) in a dose higher than 1 mg/s.c. in combination with dacarbazine and/or Interferon alpha; for preparing a medicament for the treatment of malignant melanoma on stage IV characterized by distant unresectable metastases, was not known in the art.

DESCRIPTION OF THE INVENTION

It has now been found that relatively high doses of thymosin alpha 1 in combination with dacarbazine, and optionally Interferon alpha, are useful for treating malignant melanoma on stage IV characterized by distant unresectable metastases, particularly on patients having normal serum level of LDH (lactate dehydrogenase).

For purposes of the present invention, the phrase "relatively high doses" as it pertains to thymosin alpha 1 shall be understood to mean doses in excess of about 1 mg per parenteral, e.g. subcutaneous, administration.

For purposes of the present invention, the phrase "low serum level of LDH (lactate dehydrogenase)" shall be understood to mean levels below about 460 U/L (normal levels are from 96 to 460 U/L).

It is therefore an object of the present invention to provide a use of thymosin alpha 1 in a dose higher than 1 mg/day/s.c., in combination with dacarbazine, and optionally Interferon alpha, for preparing a medicament for the treatment of malignant melanoma on stage IV characterized by distant unresectable metastases;

in which:

thymosin alpha 1 is administered in a dose from 1.1 to 7 mg/day/s.c.; the preferred dose is from 1.6 to 6.4 mg/day/s.c.; the most preferred dose are 1.6; 3.2; and 6.4 mg/day/s.c.;

dacarbazine is administered in a dose from 500 to 1100 mg/m$^2$/day/i.v.; the preferred dose is 800 mg/m$^2$/day/i.v.; and Interferon alpha is administered in a dose from 2 to 4 MIU/day/s.c.; the preferred dose is 3 MIU/day/s.c.

In still further aspects of the invention there are provided methods of treating malignant melanoma in patients requiring the same. In one embodiment, the method includes administering a combination of thymosin alpha 1 and dacarbazine, and optionally Interferon alpha, to a patient in need thereof. As administered herein, the combination of thymosin alpha 1 and dacarbazine in the amounts described herein provide therapeutic advantages over the administration of either agent alone or prior art combinations of the ingredients in the treatment of melanomas, including malignant melanomas. Those of ordinary skill will appreciate that although the methods described herein speak of combinations of the two primary therapeutic agents, it is contemplated that each of the therapeutic agents can and preferably will be administered to the patient separately rather than as part of a single pharmaceutical dosage form or even simultaneously to the patient in need thereof.

It will also be understood that the inventive methods of use and treatment contemplate administration of the synergistic combinations as part of treatment protocols as such protocols are understood by those of ordinary skill. Without wishing to be bound by particulars, such treatment protocols can call for administration of the combinations according to a schedule which can be repeated, as needed. See, for example, the 28 day cycle described in Example 1 below. Further cycles and protocols will be apparent to those of ordinary skill based upon the description provided herein and clinical expense, without undue experimentation. Other protocols for treating malignant melanoma in a patient, include administering a synergistic combination of thymosin alpha 1 and dacarbazine to patient in need thereof, wherein the combination is administered according to a protocol in which the dacarbanize is administered on day 1 thereof and the thymosin alpha 1 is administered between about one week and about two weeks thereafter. An alternative protocol for treating malignant melanoma in a patient includes administering a synergistic combination of thymosin alpha 1, dacarbazine and Interferon alpha to patient in need thereof, wherein the combination is administered according to a protocol in which the dacarbazine is administered on day 1 thereof, the thymosin alpha 1 is administered about between one week and about two weeks thereafter and the Interferon alpha is administered about 10-12 days and optionally about 18 days after the dacarbazine is administered.

A still further aspect of the invention includes a kit for treating melanomas such as malignant melanoma. The kits include effective amounts of thymosin alpha 1, dacarbazine, and optionally Interferon alpha.

Since the present invention relates in certain embodiments to using a combination of active ingredients wherein the active ingredients may be administered separately, the invention also relates to combining separate pharmaceutical compositions in kit form. That is, a kit is contemplated wherein the two principal agents, i.e. thymosin alpha 1 and dacarbazine are present, as described above. The kit will preferably include directions for the administration of the separate components. The kit form is particularly advantageous when the separate components can be administered in different dosage forms (e.g., oral and parenteral) or are administered at different dosage intervals as will most commonly be the case herein where the components are administered on different days.

For purposes of the present invention "effective amount" shall be understood to mean an amount which achieves a desired clinical result, i.e. reduction, slowing, remission, etc. or reversal of the malignant melanoma condition in the patient, i.e. mammal or human.

EXAMPLES

The following examples further illustrates the invention but are not meant in any way to restrict the effective scope of the invention.

Example 1

Phase II Clinical Trial with Dacarbazine (DTIC) Plus Thymosin Alpha 1 (Tα1) with or without Interferon Alpha (IFNα) vs DTIC Plus IFNα in Stage IV Melanoma Characterized by Distant Unresectable Metastases Trial Design phase II, randomized, stratified, open-study testing different doses of Tα1 in association with DTIC and IFNα, as first line therapy for stage IV melanoma patients characterized by distant unresectable metastases (AJCC; Journal of Clinical Oncology 2001, 19: 3635-3648) without brain metastases. The primary study end-point was tumor response, and the following combination composition were used:

DTIC (800 mg/m$^2$)+IFNα (3 MIU)+Tα1 (1.6 mg) (97 pts);
DTIC (800 mg/m$^2$)+IFNα (3 MIU)+Tα1 (3.2 mg) (97 pts);
DTIC (800 mg/m$^2$)+Tα1 (3.2 mg) (98 pts);
DTIC (800 mg/m$^2$)+IFNα (3 MIU) (94 pts);

During a preliminary analysis on 142 patients surprisingly and unexpectedly it was discovered that a clear dose-response effect was observed at the higher doses of Tα1.

The protocol was than amended and the following new group of 97 patients treated with a higher dose of Tα1 was added:

DTIC (800 mg/m$^2$)+IFNα α (3 MIU)+Tα1 6.4 mg (97).

The five groups were analyzed independently one another within the so-called "pick the winner" strategy.

Methods: Recycling every 28 days, patients were administered DTIC (800 mg/m$^2$) i.v. at day 1, Tα1 (1.6, 3.2 or 6.4 mg) s.c. at days 8-11 and 15-18, and IFNα (3 MIU) s.c. at day 11 and 18. Clinical response was evaluated every two cycles according to RECIST criteria (New Guidelines to Evaluate the Response to Treatment in Solid Tumors; Journal of the National Cancer Institute, 2000. 92: 205-216) utilizing a central reader.

The randomized patients were stratified according to the disease site: M1a, M1b or M1c level.

1) Patients with cutaneous, subcutaneous and/or limphnodal metastases with normal serum LDH value (from 96 to 460 U/L) were classified as M1a.

2) Patients with lung metastases and normal serum LDH value were classified as M1b.

3) Patients with other visceral metastases and/or with serum LDH value out of normal range were classified as M1c.

M1b patients notoriously have worse prognosis than M1a patients while the M1c patients have the worst prognosis.

It has to be emphasized that, at the time of the preliminary analysis, the distribution of the patients population among strata was as follows: 16% M1a, 25% M1b, 59% M1c. Therefore, this population is very similar to the one for which only 5% of DTIC efficacy has been found in literature in the most recent publications: Journal of Clinical Oncology, 2004, 22: 1118-1125; Journal of Clinical Oncology, 2004 ASCO Annual Meeting Proceedings (Post-Meeting Edition), 22, No 14S (July 15 Supplement): 7543); Journal of Clinical Oncology, 2004 ASCO Annual Meeting Proceedings (Post-Meeting Edition), 22, No 14S (July 15 Supplement): 7505; Journal of Clinical Oncology, 2004 ASCO Annual Meeting Proceedings (Post-Meeting Edition), 22, No 14S (July 15 Supplement): 7508). This distribution was maintained the same at the end of the recruitment.

Furthermore, according to the RECIST criteria (the most widely used criteria to evaluate response to the treatment in solid tumors) overall responses (OR) have to be confirmed after at least 4 weeks: if not confirmed, patient is considered as being in a stable disease (SD) condition.

Patients were treated with up to 6 cycles, unless one of the following three conditions appeared:

1) Development of any serious adverse event (SAE), unexpected worsening of the patient's basal conditions which would make participation in the trial inappropriate;

2) Progression of disease;

3) Withdrawal by patient of the consent to participate to the trial.

In all these cases, the patients were withdrawn from the study.

Patients who, at the end of the 6 cycles, were in SD, Partial Response (PR) or Complete Response (CR), could be treated further on, according to the Physician's opinion, until a maximum of 24 cycles.

The results of a clinical trial, reported in the following Tables 1/A-5/A relate to patients treated without considering their LDH serum levels.

The results obtained, reported in the following Tables 1/B-5/B relates to patients with a serum level of LDH between 96 to 460 U/L (this is a sub population of the patients treated/present in Tables 1/A-5/A.

TABLE 1/A

Dacarbazine (800 mg/m$^2$) + IFNα Interferon alpha (3 MIU) (control group)

| | RESULTS |
|---|---|
| Patients Evaluated | 94 |
| Complete Response Rate | 0 |
| Partial Response Rate | 5 |
| Complete Response Rate + Partial Response Rate | 5 (5.3%) |

TABLE 1/B

Dacarbazine (800 mg/m$^2$) + IFNα Interferon alpha (3 MIU) (control group)

| | RESULTS EXCLUDING ELEVATED LDH |
|---|---|
| Patients Evaluated | 62 |
| Complete Response Rate | 0 |
| Partial Response Rate | 3 |
| Complete Response Rate + Partial Response Rate | 3 (4.8%) |

TABLE 2/A

Dacarbazine (800 mg/m$^2$) + IFNα Interferon alpha (3 MIU) + Thymosin alpha 1 (1.6 mg)

| | RESULTS |
|---|---|
| # of Patients Evaluated | 97 |
| Complete Response Rate | 2 |
| Partial Response Rate | -5 |
| Complete Response Rate + Partial Response Rate | 7 (7.2%) |

TABLE 2/B

Dacarbazine (800 mg/m$^2$) + IFNα Interferon alpha (3 MIU) + Thymosin alpha 1 (1.6 mg)

|  | RESULTS EXCLUDING ELEVATED LDH |
|---|---|
| # of Patients Evaluated | 64 |
| Complete Response Rate | 2 |
| Partial Response Rate | 5 |
| Complete Response Rate + Partial Response Rate | 7 (10.9%) |

TABLE 3/A

Dacarbazine (800 mg/m$^2$) + Interferon alpha (3 MIU) + Thymosin alpha 1 (3.2 mg)

|  | RESULTS |
|---|---|
| # of Patients Evaluated | 97 |
| Complete Response Rate | 2 |
| Partial Response Rate | 8 |
| Complete Response Rate + Partial Response Rate | 10 (10.3%) |

TABLE 3/B

Dacarbazine (800 mg/m$^2$) + Interferon alpha (3 MIU) + Thymosin alpha 1 (3.2 mg)

|  | RESULTS EXCLUDING ELEVATED LDH |
|---|---|
| # of Patients Evaluated | 58 |
| Complete Response Rate | 2 |
| Partial Response Rate | 6 |
| Complete Response Rate + Partial Response Rate | 8 (13.8%) |

TABLE 4/A

Dacarbazine (800 mg/m$^2$) + Interferon alpha (3 MIU) + Thymosin alpha 1 (6.4 mg)

|  | RESULTS |
|---|---|
| # of Patients Evaluated | 97 |
| Complete Response Rate | 2 |
| Partial Response Rate | 4 |
| Complete Response Rate + Partial Response Rate | 6 (6.2%) |

TABLE 4/B

Dacarbazine (800 mg/m$^2$) + Interferon alpha (3 MIU) + Thymosin alpha 1 (6.4 mg)

|  | RESULTS EXCLUDING ELEVATED LDH |
|---|---|
| # of Patients Evaluated | 62 |
| Complete Response Rate | 2 |
| Partial Response Rate | 4 |
| Complete Response Rate + Partial Response Rate | 6 (9.7%) |

TABLE 5/A

Dacarbazine (800 mg/m$^2$) + Thymosin alpha 1 (3.2 mg)

|  | RESULTS |
|---|---|
| # of Patients Evaluated | 98 |
| Complete Response Rate | 2 |
| Partial Response Rate | 11 |
| Complete Response Rate + Partial Response Rate (%) | 13 (13.3%) |

TABLE 5/B

Dacarbazine (800 mg/m$^2$) + Thymosin alpha 1 (3.2 mg)

|  | RESULTS EXCLUDING ELEVATED LDH |
|---|---|
| # of Patients Evaluated | 59 |
| Complete Response Rate | 2 |
| Partial Response Rate | 9 |
| Complete Response Rate + Partial Response Rate (%) | 11 (18.6%) |

The results reported in Tables 1/A-5/A surprisingly, and unexpectedly, show that the combination according to the invention is therapeutically more active than DITIC in combination with IFNα.

In fact the control group shows a response of 5.3% (Table 1/A) while the other groups show a response from 6.2 (table 4/A) to 13.3% (table 5/A).

These results were confirmed in the sub population composed of patients without an elevated baseline level of serum LDH. In fact the control group shows a response of 4.8% (Table 1/B while the other groups show a response from 9.7 (table 4/B) to 18.6% (table 5/B).

For a pathology in which: (a) DTIC is the only chemotherapeutic agent approved, (b) the actual overall responses to DTIC are 5.5-6.8%, and (c) there is no evidence that these responses have any effect on the patients' overall survival; the results above reported have shown a really surprisingly unexpected therapeutic effect.

The daily dose of the active ingredients to be administered will depend, according to the judgement of the primary care physician, on the subject's weight, age or general condition.

Thymosin alpha 1, dacarbazine and Interferon alpha are well known active ingredients used in the medical field.

The invention claimed is:

1. A method of treating stage IV malignant melanoma classified as M1a, M1b or M1c, consisting of administering: thymosin alpha 1 in a dose of 6.4 mg/day/s.c., in combination with an effective amount of dacarbazine, to a human with stage IV malignant melanoma classified as M1a, M1b or M1c.

2. Method according to claim 1, in which dacarbazine is administered in a dose from 500 to 1100 mg/m$^2$/day/i.v.

3. Method according to claim 1, in which dacarbazine is administered in a dose of 800 mg/m$^2$/day/i.v.

4. Method according to claim 1, in which the human to be treated has a normal serum level of LDH.

5. A method of treating malignant melanoma in a human patient, consisting of administering a synergistic combination of thymosin alpha 1 and dacarbazine to a patient with stage IV malignant melanoma classified as M1a, M1b or M1c, wherein said combination is administered according to a protocol in which the dacarbazine is administered in a dose of 800 mg/m$^2$/day/i.v., on day 1 thereof and the thymosin alpha 1 is administered in a dose of 6.4 mg/day/s.c. about one week and about two weeks thereafter.

6. Method according to claim 5, in which the human to be treated has a normal serum level of LDH.

* * * * *